US00PP13141P2

(12) United States Plant Patent
Manichote

(10) Patent No.: US PP13,141 P2
(45) Date of Patent: Oct. 29, 2002

(54) AGLAONEMA PLANT NAMED 'SIAM MAJESTY'

(75) Inventor: Pichai Manichote, Bangkok (TH)

(73) Assignee: Ladda Co., LTD, Bangkok (TH)

( * ) Notice: Subject to any disclaimer, the term of this patent is extended or adjusted under 35 U.S.C. 154(b) by 0 days.

(21) Appl. No.: 09/706,897

(22) Filed: Nov. 6, 2000

(51) Int. Cl.[7] ..... A01H 5/00

(52) U.S. Cl. ..... Plt./376

(58) Field of Search ..... Plt./376

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new and distinct cultivar of Aglaonema named 'Siam Majesty' characterized by red venation on dark green ovate leaves, compact, and well-branched growth habit.

3 Drawing Sheets

BACKGROUND OF THE INVENTION

The present invention is directed to a new and distinct cultivar of Aglaonema, botanically known as *Aglaonema hybrids,* and having the cultivar name 'Siam Majesty.'

The new cultivar was discovered as a seedling among progeny of Aglaonema 'Giant' grown in a cultivated area in Prachub Kireekan, Thailand. It is presumed to be a hybrid of *Aglaonema rotundum* 'Giant' and a native species that thrives in an adjacent area.

Asexual propagation of the new cultivar in Nakhon Pathom, Thailand, by vegetative cuttings has demonstrated the uniformity and the stability through successive generations of this new Aglaonema.

SUMMARY OF THE INVENTION

The following traits have been repeatedly observed in the new cultivar grown from top cuttings under 50% shade conditions in Nakhon Pathom, Thailand, which closely approximate those commonly used in commercial horticultural practice.

The features that in combination are believed to distinguish 'Siam Majesty' from other known cultivars of Aglaonema include: compact growth habit with freely branching, dense and upright growth; ovate leaves; adaxial leaf surfaces having dark, glossy green color with red mid-rib and veins. Plants of the new Aglaonema can be compared to plants of the *Aglaonema rotundum* 'Giant' (not patented) which are commonly grown in Asia. Plants of the new Aglaonema cultivar 'Siam Majesty' differ from plants of the cultivar 'Giant' in the following characteristics:

1. Plants of the new Aglaonema are more erect, taller and more bushy than those of the 'Giant' cultivar;

2. The mid-rib veins of the new Aglaonema are red instead of pink, as is found in 'Giant' cultivar;

3. The leaf shape of the new Aglaonema is ovate, while that of the 'Giant' cultivar is broadly ovate; and 4. Sheaths of the new Aglaonema do not prolong (i.e., ligule absent) as in the 'Giant' cultivar.

BRIEF DESCRIPTION OF ILLUSTRATIONS

The accompanying color photographs illustrate the overall appearance of the new cultivar as true in color as possible in color illustrations of this type.

DETAILED DESCRIPTION

All color reference are in accordance with The Royal Horticultural Society Colour Chart (1995 ed). Colors are approximate as color depends on climate and environmental condition.

Botanical classification: *Aglaonema hybrid* 'Siam Majesty.'
Parentage:
- *Female parent.*—*Aglaonema rotundum* 'Giant.'
- *Male parent.*—Unknown; possibly *Aglaonema simplex* or *Aglaonema tenuipes.*

Figure 1:
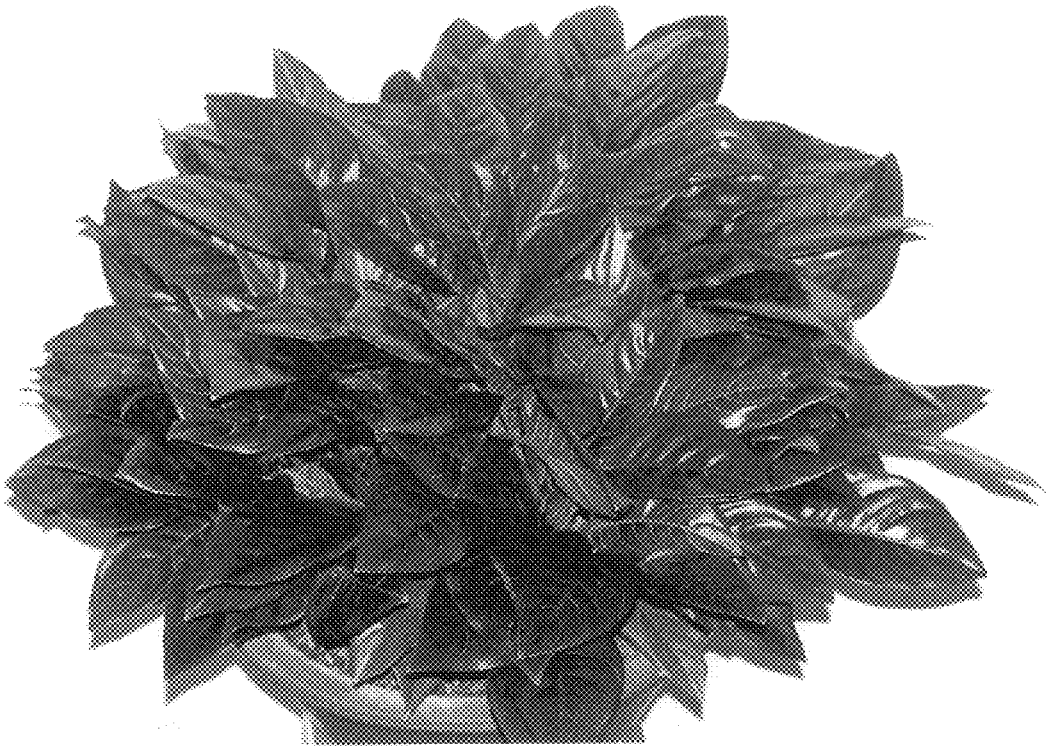
FIG. 1 is a top perspective view of a single plant of 'Siam Majesty' in a 45 cm container about 15 months after planting.
Figure 2:
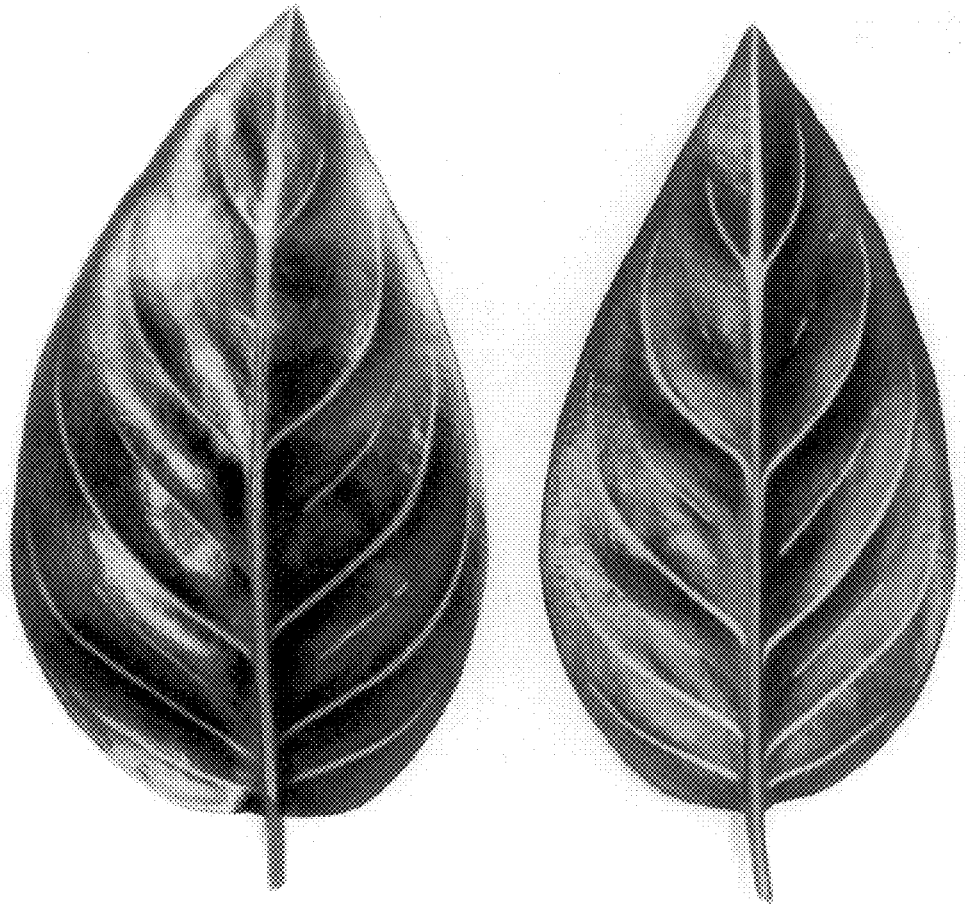
FIG. 2 is a view of adaxial surface (left) and abaxial surface (right) of mature leaves.
Figure 3:
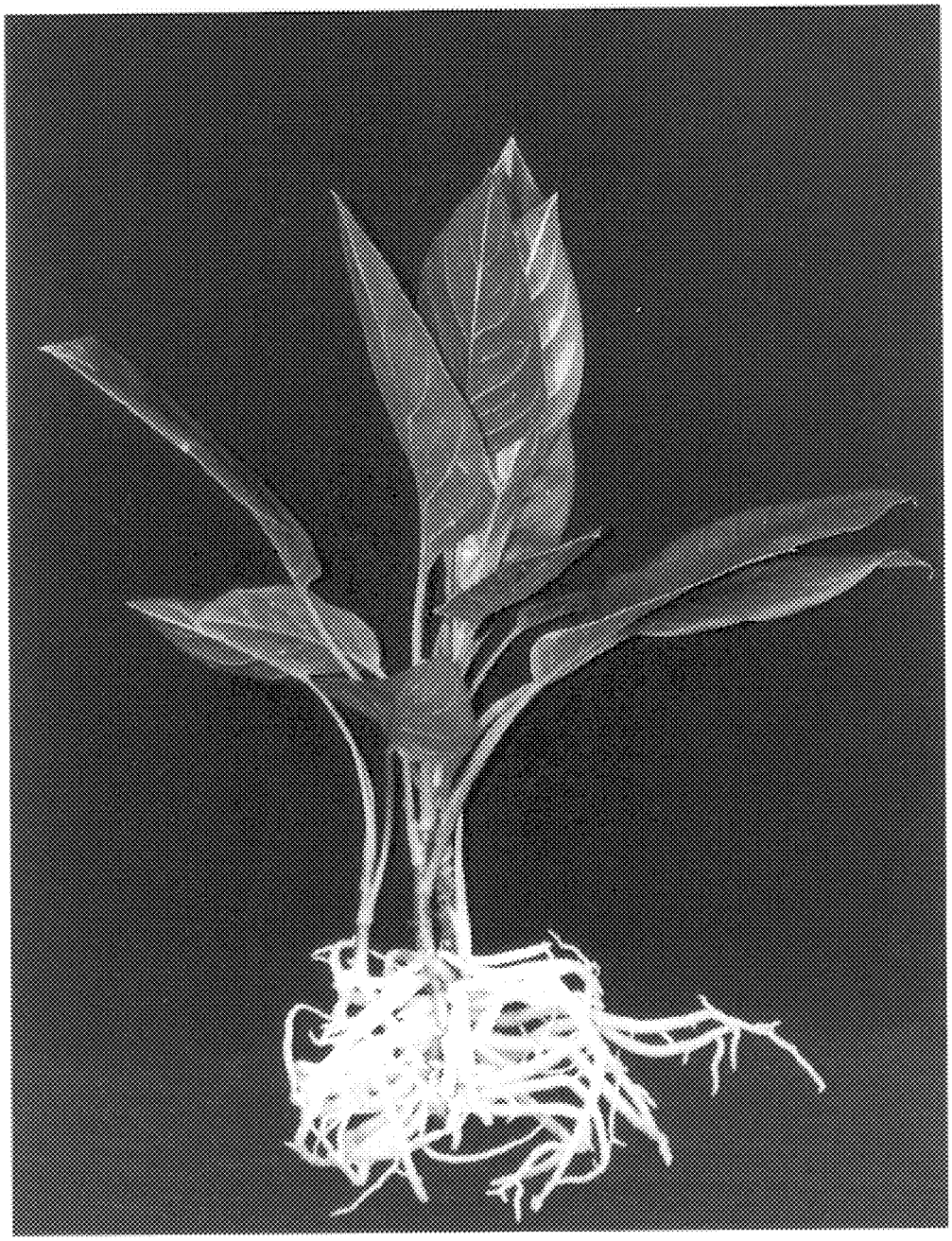
FIG. 3 illustrates the root development, after 3 month of cutting.

Propagation: By top cuttings, stem cuttings, and by division. Root initiation: within 3 weeks. No fruit setting.
Plant description:
- *Plant shape.*—Upright and outwardly spreading, symmetrical, dense and compact.
- *Growth habit.*—Erect when young, becoming more outwardly arching and spreading as plant develops.
- *Plant size.*—Height from soil surface to top of leaf canopy: about 15 to 20 cm. Width: about 20 to 25 cm.
- *Root description.*—Very thick white storage roots with fine laterals, as shown in FIG. 3.
- *Plant vigor.*—Vigorous, rapid growth rate.
- *Foliage description.*—Leaf shape: Ovate with an acute apex, an obtuse base, and an entire margin; symmetric leaf blade; leaf length: about 13.0 to 14.6 cm; leaf width: about 7.0 to 9.0 cm. Venation: pinnate, strongly differentiated into 5 pairs of primary veins, diverging from midrib at 40 to 75°. Leaf surface: Smooth and waxy but convex between the primary veins. Leaf aspect: Erect initially, eventually horizontal to the stem. Leaf color: Young leaf: upper surface near 141A, mid-rib and veins near 57A; lower surface near 152A, mid-rib and veins near 68C. Mature leaf: upper surface near 139A, mid-rib and veins near 139A; lower surface near 137B; mid-rib and veins near 196C. Petiole: Length about 5.0 to 6.0 cm; color near 139A.

*Inflorescence*.—Typical of Aglaonema. Peduncle: Solitary, rarely two together, length 3.5 to 7.6 cm. Cataphylls: Length to 7 cm. Spathe: Gibbous; length about 3.2 cm; often apiculate. Stipe: Length about 0.3 cm. Spadix: Clavate, with length to about 2.7 cm; spadix tip almost equal or slightly exceeding spathe tip; pistillate portion about 0.4 cm long, with 14 pistils; staminode 3 rolls; staminate portion about 2.3 cm long and 1.2 cm thick.

Plants of the Aglaonema cultivar 'Siam Majesty' are dense, compact and have upright growth habit. The upper leaf surfaces are plain dark green with red mid-rib and veins. The leaves are ovate in shape with acute apex. White storage roots are present.

I claim:

1. A new and distinct plant of Aglaonema named 'Siam Majesty' substantially as illustrated and described.

* * * * *